US00PP15045P3

(12) United States Plant Patent
Danziger

(10) Patent No.: US PP15,045 P2
(45) Date of Patent: Jul. 27, 2004

(54) CHRYSANTHEMUM PLANT NAMED 'DANCHRYAT'

(50) Latin Name: *Chrysanthemum morifolium*
Varietal Denomination: Danchryat

(75) Inventor: Gabriel Danziger, Nir-Zvi (IL)

(73) Assignee: Danziger "Dan" Flower Farm, Moshav Mishmar Hashiva (IL)

( * ) Notice: Subject to any disclaimer, the term of this patent is extended or adjusted under 35 U.S.C. 154(b) by 0 days.

(21) Appl. No.: 10/230,302

(22) Filed: Aug. 29, 2002

(65) Prior Publication Data

US 2004/0045064 P1 Mar. 4, 2004

(51) Int. Cl.[7] ..... A01H 5/00
(52) U.S. Cl. ..... Plt./294
(58) Field of Search ..... Plt./294

*Primary Examiner*—Howard J. Locker
(74) *Attorney, Agent, or Firm*—Foley & Lardner LLP

(57) ABSTRACT

A new and distinct Chrysanthemum plant named 'Danchryat' characterized by having white, oblong shaped ray florets and yellow bell shaped disc florets; flowering time 7.5 weeks; short day plant; and vigorous growth habit.

1 Drawing Sheet

Genus and species of the claimed plant: *Chrysanthemum morifolium.*
Variety denomination: Danchryat.
Commercial: Chrysanthemum cv. 'Atlantis'.

BACKGROUND OF THE INVENTION

The present invention relates to a new and distinct cultivar of Chrysanthemum plant, botanically known as *Chrysanthemum morifolium,* hereinafter referred to by the cultivar name 'Danchryat'.

The new cultivar originated from a cross made in a controlled breeding program in Moshav Mishmar Hashiva, Israel. The female parent is chf52 of our breeding program (unpatented). The male parent is an unnamed open pollinated Chrysanthemum (unpatented).

'Danchryat' was discovered and selected by the inventor, Gabriel Danziger, as a flowering plant within the progeny of the stated cross in a controlled environment in Moshav Mishmar Hashiva, Israel.

'Danchryat' was selected in a cultivated environment in Moshav Mishmar Hashiva, Israel. Asexual reproduction of the new cultivar by stem cutting was first performed in January 1999 in Moshav Mishmar Hashiva, Israel and has demonstrated that the combination of characteristics as herein disclosed for the new cultivar are firmly fixed and retained through successive generations of asexual reproduction.

BRIEF SUMMARY OF THE INVENTION

The following traits have been repeatedly observed and are determined to be basic characteristics of 'Danchryat' which in combination distinguish this Chrysanthemum as a new and distinct cultivar:

1. White, oblong shaped ray florets and yellow bell shaped disc florets;
2. flowering time 7.5 weeks;
3. short day plant; and
4. vigorous growth habit.

'Danchryat' has not been observed under all possible environmental conditions. The phenotype of the new cultivar may vary significantly with variations in environment such as temperature, light intensity, and daylength without any change in the genotype of the plant. The flowering observations, measurements and values describe the new cultivar as grown in Moshav Mishmar Hashiva, Israel under conditions which closely approximate those generally used in commercial practice.

Of the many commercial cultivars known to the present inventor, the most similar in comparison to 'Danchryat' is the cultivar 'White Elite Reagan' (U.S. Published Application No. 20030046741, Ser. No. 09/902,967).

| Characteristic | 'Danchryat' | 'White Elite Reagan' |
|---|---|---|
| Flower Size | 9.5 cm. | 8.5 cm. |
| Flowering time | 7.5 weeks | 8.5–9 weeks |
| Growth Potency | Medium-High | Medium-High |

BRIEF DESCRIPTION OF THE DRAWING

The accompanying photographic drawing illustrates the overall appearance of the new Chrysanthemum showing the colors as true as is reasonably possible with color reproduction of this type.

The drawing shows a side-view of the inflorescences and foliage of 'Danchryat'.

DETAILED BOTANICAL DESCRIPTION

The following observations, measurements and values describe the new cultivar as grown in Moshav Mishmar Hashiva, Israel under conditions which closely approximate those generally used in commercial practice. Irrigate and fertilize on regular basis at a recommended temperature range of 22–23 degrees Celsius. Mainly grown in greenhouses, can also be grown outdoors during summer. Color references are made to The Royal Horticultural Society Colour Chart (R.H.S.), except where general colors of ordinary significance are used. Color values were taken under daylight conditions at approximately 12:00 pm. in Moshav Mishmar Hashiva, Israel. The age of the plant described is 11 weeks from planting.

Propagation: Stem cutting.

Plant:

*General appearance and form.*—Height: 90 cm. Width: 20 cm. Shape: Corymb. Flowering response: Short day type. Flowering season: Naturally flowers during late autumn (November) into winter. Winter hardiness: Hardy in moderate climate. Lastingness of the individual bloom: 3–3.5 weeks. Rooting habit: Adventitious roots from cutting base. Time to initiate roots: 6–7 days. Fragrance: None.

Foliage:

*Overall shape of leaf.*—Pinnatipartite.

*Base shape.*—Wedge-shaped.

*Apex shape.*—Rounded.

*Margin.*—Serrate.

*Texture.*—Slightly warty.

*Leaf length.*—10 cm.

*Leaf width.*—5.5 cm.

*Color of upper surface.*—Mature leaf: Yellow-green 147-A. Immature leaf: Yellow-green 147-A.

*Color of lower surface.*—Mature leaf: Yellow-green 147-B. Immature leaf: Yellow-green 147-B.

*Venation color.*—Upper surface: Yellow-green 147-B. Lower surface: Yellow-green 147-C.

*Petiole.*—Length: 2 cm. Diameter: 4 mm. Color: Yellow-green 146-A.

Inflorescence:

*Flowering response.*—Short day.

*Quantity of inflorescences.*—7–8 flowers, on average, per stem.

*Inflorescence bud.*—Height: 1 cm. Diameter: 16 mm. Color: Yellow-green 146-B.

*Inflorescence size.*—Diameter: 9.5 cm. Depth (height): 18–20 mm. Diameter of disc: 18 mm.

*Ray florets.*—Shape: Oblong. Length: 35–40 mm. Width: 12–13 mm. Apex: 6–8 mm. Margin: Entire. Texture: Smooth. Number of ray florets per inflorescence: 30–32. Color when opening: White 155-D. Color when fully opened upper surface: White 155-D. Color when fully opened lower surface: White 155-C.

*Disc florets.*—Shape: Bell shaped (campanulate). Length: 4–5 mm. Width: 1 mm. Apex: Toothed. Margin: Entire. Texture: Smooth. Number of disc florets per inflorescence: 200–220. Color when opening: Yellow-green 146-B. Color when fully opened upper surface: Yellow 9-A. Color when fully opened lower surface: Yellow 9-C.

*Stem.*—Average length: 85–90 cm. Average diameter: 8–10 mm. Color: Yellow-green 146-B. Branching characteristics: One branch occurs naturally; additional breaks occur responsive to pinching. Internode length: 15–20 mm.

*Peduncles.*—Length: 10–15 cm, 15 cm on average. Diameter: 3.5–4 mm. Texture: Slightly warty. Color: Yellow-green 146-B.

Reproductive organs:

*Stamen.*—Number: 5 fused as a tube. Color: Yellow 13-A.

*Seeds.*—Achene. Width: 0.8–1 mm. Length: 1.5 mm. Shape: Achene. Color: Grayed-green 197-A.

*Anthers.*—Yellow 13-A.

*Pollen.*—Yellow 13-A.

*Stigma.*—Yellow 12-B.

*Ovary.*—Yellow-green 149-D.

Disease resistance: No susceptibility was observed under regular growing condition.

I claim:

1. A new and distinct Chrysanthemum plant named 'Danchryat', substantially as illustrated and described herein.

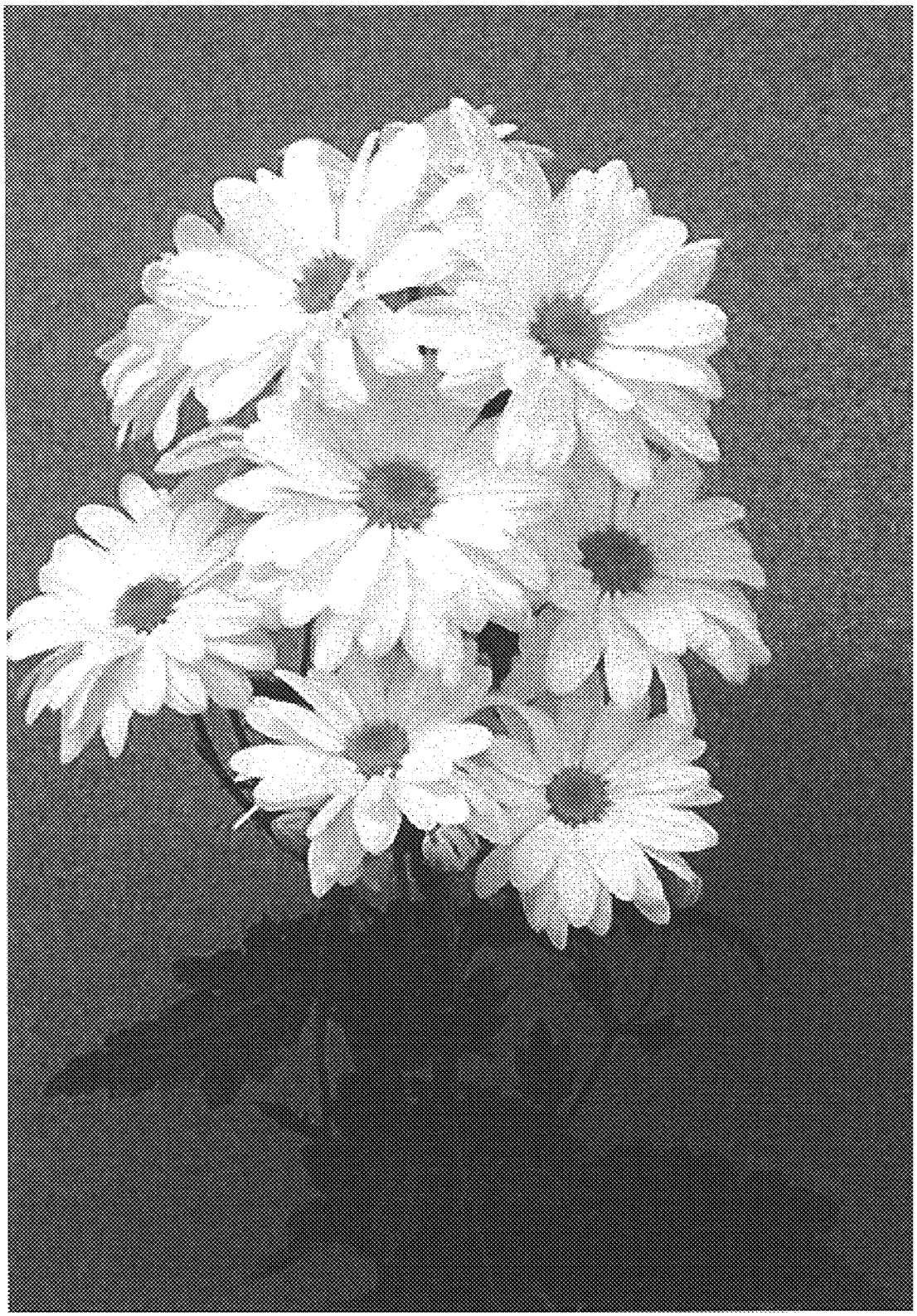

* * * * *